United States Patent [19]

Borland et al.

[11] Patent Number: 4,801,426

[45] Date of Patent: Jan. 31, 1989

[54] AMINE DEODORIZATION

[75] Inventors: James E. Borland; Joe D. Sauer, both of Baton Rouge, La.

[73] Assignee: Ethyl Corporation, Richmond, Va.

[21] Appl. No.: 9,229

[22] Filed: Jan. 30, 1987

[51] Int. Cl.$^4$ .............................................. A61L 2/20
[52] U.S. Cl. ......................................... 422/5; 210/749
[58] Field of Search ............................ 422/5; 210/749

[56] References Cited

U.S. PATENT DOCUMENTS 4,144,122  3/1979  Emanuelsson et al. .............. 162/158

FOREIGN PATENT DOCUMENTS 1120697  6/1986  Japan ........................................ 422/5

OTHER PUBLICATIONS

CA 90(20): 156468c, 1978.

Primary Examiner—Barry S. Richman
Assistant Examiner—Jill Johnston
Attorney, Agent, or Firm—J. D. Odenweller

[57] ABSTRACT

Malodorous aliphatic amines are de-odorized by injecting nitrogen gas into the liquid phase while maintaining the liquid temperature at about 30°–100° C.

9 Claims, No Drawings

AMINE DEODORIZATION

BACKGROUND

Aliphatic amines are used as chemical intermediates and are especially useful in detergent and cosmetic formulations. When used in consumer products it is essential that the amines do not introduce an objectionable odor. As manufactured, higher aliphatic amines generally have an unpleasant odor developed during the manufacturing process. A need exists for a simple inexpensive way to reduce or eliminate this odor.

SUMMARY

It has now been discovered that malodorous aliphatic amines can be de-odorized to make them acceptable for use in consumer oriented products by injecting gaseous nitrogen into the liquid aliphatic amine, preferably while held at an elevated temperature. This method has a distinct advantage over other methods that involve the addition of masking agents or chemical treatment in that it does not introduce any new chemical into the amine which would require further approval of Federal agencies. Furthermore, the new method is simple and inexpensive to conduct.

DESCRIPTION OF THE PREFERRED EMBODIMENTS

A preferred embodiment of the invention is a process for de-odorizing a malodorous aliphatic amine which contains about 8–40 carbon atoms by injecting nitrogen gas into the amine for a period of time sufficient to decrease the malodor to an acceptable level.

The process is conducted on higher aliphatic amines. These are amines which contain at least 8 carbon atoms such as octylamine, dodecylamine, eicosylamine, tetracosylamine, triacontylamine and the like. More preferably the amine is an aliphatic tertiary amine. One class of such amines which are used in detergent and cosmetic formulations are the $C_{6-22}$ alkyl di-$C_{1-2}$ alkylamines such as n-hexyl diethylamine, n-octyl dimethylamine, 2-ethylhexyl diethylamine, n-tetradecyl dimethylamine and the like. Of this class the more useful amines are the $C_{8-20}$ alkyl dimethylamines such as n-octyl dimethylamine, n-decyl dimethylamine, n-dodecyl dimethylamine, n-octadecyl dimethylamine, n-docosyl dimethylamine and the like.

Another very useful class of aliphatic tert-amines are the di-($C_{6-22}$ alkyl) $C_{1-2}$ alkyl amines such as dihexyl ethylamine, hexyl decyl methylamine, dodecyl tetradecyl ethylamine, dieicosyl methylamine, and the like. Of this class, the more useful amines are the di($C_{8-20}$ alkyl)methylamines such di-n-octyl methylamine, di-n-tetradecyl methylamines, di-n-tetradecyl methylamine, di-n-octadecyl methylamine, di-n-eicosyl methylamine, n-hexadecyl n-octadecyl methylamine and the like.

The de-odorization is carried out by injecting gaseous nitrogen into the liquid amines until the odor is reduced to an acceptable level. The rate of nitrogen injection does not seem to be critical and depends upon the equipment available. The vent gas is preferably treated to remove any chemicals in it prior to release to the atmosphere. For example, the vent gas can be passed through an acid scrubber (e.g., sulfuric acid or phosphoric acid). If desired the vent gas can then be passed through a drying column and recycled to the crude amine vessel. Concentrated sulfuric acid can act as both scrubber and dryer.

Time required to remove the odor can be shortened by heating the amine to an elevated temperature. Temperatures up close to the amine boiling point can be used but it is preferred to hold the maximum temperature at least 25° C. below the amine boiling point. A useful temperature range is between 30° and 100° C. Excellent results have been achieved at around 50° C. Under these conditions the odor level is usually reduced to an acceptable level in about 2 hours.

Comparative tests were conducted to evaluate the de-odorization process. The amine used in all the tests was a commercial n-octadecyl dimethylamine that had not been subjected to any de-odorization procedure. The de-odorization procedures evaluated were as follows:

a. A chromatography column was packed with Baker Molecular Seive, Type 4A (8–12 mesh) to form a bed approximately ¾×8". A sample of the amine was allowed to elute through the bed to collect 75 mL for test panel comparison.

b. A chromatography column was packed with MCB Molecular Seive, Type 13X (8–12 mesh) to form a bed approximately ¾×8". A sample of the amine was allowed to elute through the bed to collect 75 mL for test panel comparison.

c. A 100 mL sample of the amine was sparged at 50° C. with a stream of nitrogen for 2 hours. This sample was utilized as is for test panel comparison.

d. A 100 mL sample of the amine was subjected to a vacuum stripping procedure (about 10 mm Hg pressure) for 2 hours at 50° C. This sample was utilized as is for test panel comparison.

e. A chromatography column was packed with Activated Charcoal (8–12 mesh) to form a bed approximately ¾×8". A sample of the amine was allowed to elute through the bed to collect 75 mL for test panel comparison.

f. A control sample of the amine was also included untreated for test panel comparison. This lot of amine was the feed material for all odor improvement experiments.

Following the treatment, each amine sample was evaluated for malodor and graded on a scale of 1 (best) to 6 (worst) by a panel of 17 evaluators. The following table gives the results of this evaluation.

| Evaluator | Deodorization Process | | | | | |
|---|---|---|---|---|---|---|
| | A | B | C | D | E | F |
| a | 2 | 3 | 4 | 5 | 1 | 6 |
| b | 2 | 5 | 1 | 6 | 3 | 4 |
| c | 6 | 3 | 1 | 4 | 2 | 5 |
| d | 1 | 2 | 4 | 5 | 3 | 6 |
| e | 4 | 1 | 5 | 3 | 6 | 2 |
| f | 4 | 5 | 1 | 3 | 2 | 6 |
| g | 4 | 5 | 2 | 3 | 1 | 6 |
| h | 4 | 5 | 1 | 3 | 2 | 6 |
| i | 1 | 3 | 2 | 5 | 6 | 4 |
| j | 4 | 1 | 3 | 5 | 2 | 6 |
| k | 1 | 3 | 4 | 6 | 2 | 5 |
| l | 3 | 2 | 4 | 5 | 1 | 6 |
| m | 4 | 2 | 1 | 6 | 5 | 3 |
| n | 5 | 1 | 3 | 4 | 2 | 6 |
| o | 5 | 4 | 1 | 6 | 2 | 3 |
| p | 4 | 2 | 1 | 5 | 3 | 6 |
| q | 5 | 2 | 1 | 3 | 4 | 6 |
| Total Score | 59 | 49 | 39 | 77 | 47 | 86 |
| Average Score | 3.47 | 2.88 | 2.29 | 4.53 | 2.76 | 5.06 |
| Standard Deviation | 1.55 | 1.45 | 1.45 | 1.18 | 1.60 | 1.34 |
| Number "Best" | 3 | 3 | 8 | 0 | 3 | 0 |

| Evaluator | Deodorization Process | | | | | |
|---|---|---|---|---|---|---|
| | A | B | C | D | E | F |
| Number "Worst" | 1 | 0 | 0 | 4 | 2 | 10 |

The tests clearly show that process C of this invention, although the simplest procedure, gave by far the best results.

We claim:

1. A process for de-odorizing a malodorous liquid phase aliphatic amine, said amine containing about 8–40 carbon atoms, said process consisting essentially of injecting a gas consisting essentially of nitrogen into said amine for a period of time sufficient to decrease the malodor to an acceptable level while maintaining said amine in the liquid phase.

2. A process of claim 1 wherein said amine is maintained at a temperature of about 30°–100° C. during said nitrogen injection.

3. A process of claim 1 wherein said amine is an aliphatic tertiary amine.

4. A process of claim 3 wherein said tert-amine is a $C_{6-22}$ alkyl di-$C_{1-2}$ alkylamine.

5. A process of claim 4 wherein said tert-amine is a $C_{8-20}$ alkyl dimethylamine.

6. A process of claim 5 wherein said tert-amine is maintained at a temperature of about 30°–100° C. during the nitrogen injection.

7. A process of claim 3 wherein said tert-amine is a di($C_{6-22}$ alkyl)$C_{1-2}$ alkylamine.

8. A process of claim 7 wherein said tert-amine is a di-$C_{8-20}$ alkyl methylamine.

9. A process of claim 8 wherein said tert-amine is maintained at a temperature of about 30°–100° C. during the nitrogen injection.

* * * * *